US010568999B2

(12) United States Patent
Gross

(10) Patent No.: US 10,568,999 B2
(45) Date of Patent: Feb. 25, 2020

(54) RECIPROCATING INTRAVASCULAR BLOOD PUMP

(71) Applicant: RAINBOW MEDICAL LTD., Herzliya (IL)

(72) Inventor: Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 49 days.

(21) Appl. No.: 15/831,973

(22) Filed: Dec. 5, 2017

(65) Prior Publication Data

US 2019/0167877 A1    Jun. 6, 2019

(51) Int. Cl.
*A61M 1/12* (2006.01)
*A61M 1/10* (2006.01)
*A61M 1/36* (2006.01)
*A61M 1/16* (2006.01)

(52) U.S. Cl.
CPC .......... *A61M 1/125* (2014.02); *A61M 1/1005* (2014.02); *A61M 1/1037* (2013.01); *A61M 1/1086* (2013.01); *A61M 1/1036* (2014.02); *A61M 1/122* (2014.02); *A61M 1/1645* (2014.02); *A61M 1/3607* (2014.02)

(58) Field of Classification Search
CPC ........ A61M 1/12; A61M 1/122; A61M 1/125; A61M 1/1041; A61M 1/1039; A61M 1/1037; A61M 1/1005
See application file for complete search history.

(56) References Cited

U.S. PATENT DOCUMENTS

| | | |
|---|---|---|
| 5,484,385 A | 1/1996 | Rishton |
| 5,693,091 A | 12/1997 | Larson, Jr. et al. |
| 5,762,599 A | 6/1998 | Sohn |
| 6,290,641 B1 | 9/2001 | Nigroni et al. |
| 7,468,050 B1 | 12/2008 | Kantrowitz |
| 7,544,160 B2 | 6/2009 | Gross |
| 7,722,568 B2 | 5/2010 | Lenker et al. |
| 7,976,452 B2 | 7/2011 | Kantrowitz |
| 8,900,191 B2 | 12/2014 | Lenker et al. |
| 2003/0032853 A1 | 2/2003 | Korakianitis et al. |
| 2016/0206798 A1* | 7/2016 | Williams ............... A61M 1/125 |

OTHER PUBLICATIONS

Communication dated Dec. 19, 2019, from the European Patent Office in counterpart European Application No. 19178111.1.

* cited by examiner

*Primary Examiner* — Suba Ganesan
(74) *Attorney, Agent, or Firm* — Sughrue Mion, PLLC

(57) ABSTRACT

Apparatus is provided for deployment in a lumen of a blood vessel of a subject. The apparatus includes a reciprocating device configured to move downstream and upstream in the blood vessel in a reciprocating pattern to provide: (i) a first effective surface area of the device for pushing blood downstream in the blood vessel during downstream motion of the reciprocating device, and (ii) second effective surface area of the device during upstream motion of the reciprocating device. The first effective surface area is larger for pushing blood in the blood vessel than the second effective surface area. The apparatus further includes a device driver configured to drive the reciprocating device in the reciprocating pattern. Other applications are also described.

5 Claims, 6 Drawing Sheets

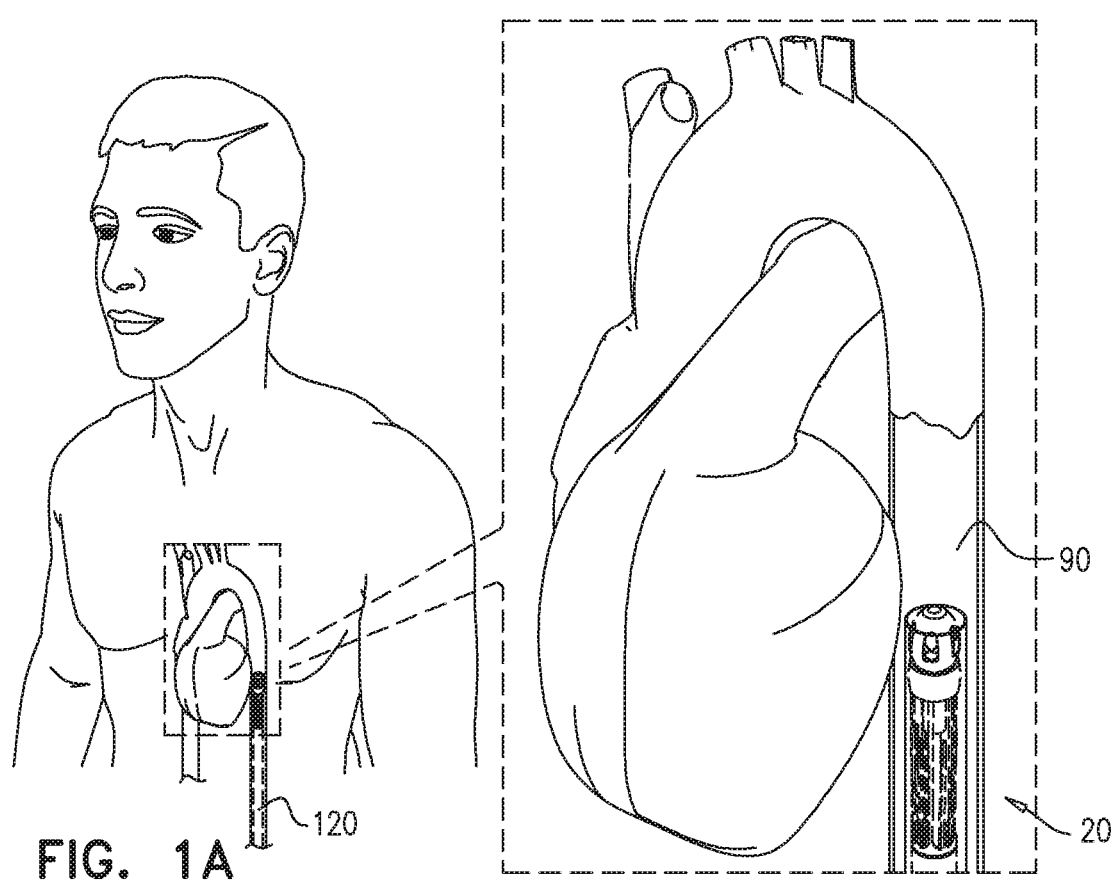
FIG. 1A
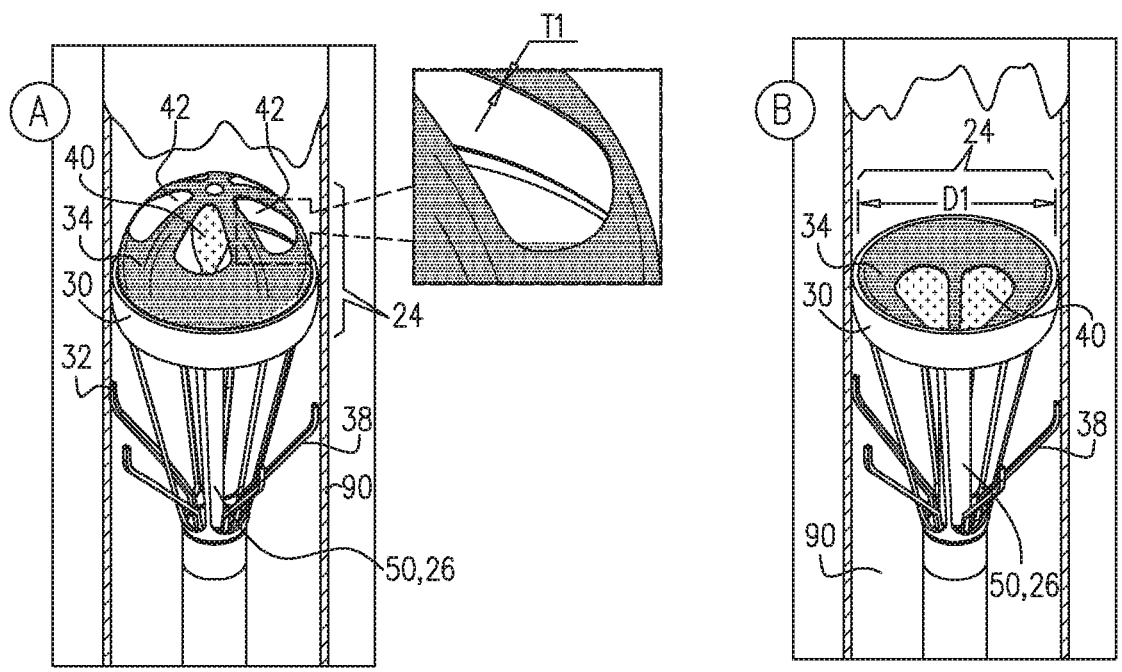
FIG. 1B
FIG. 1C

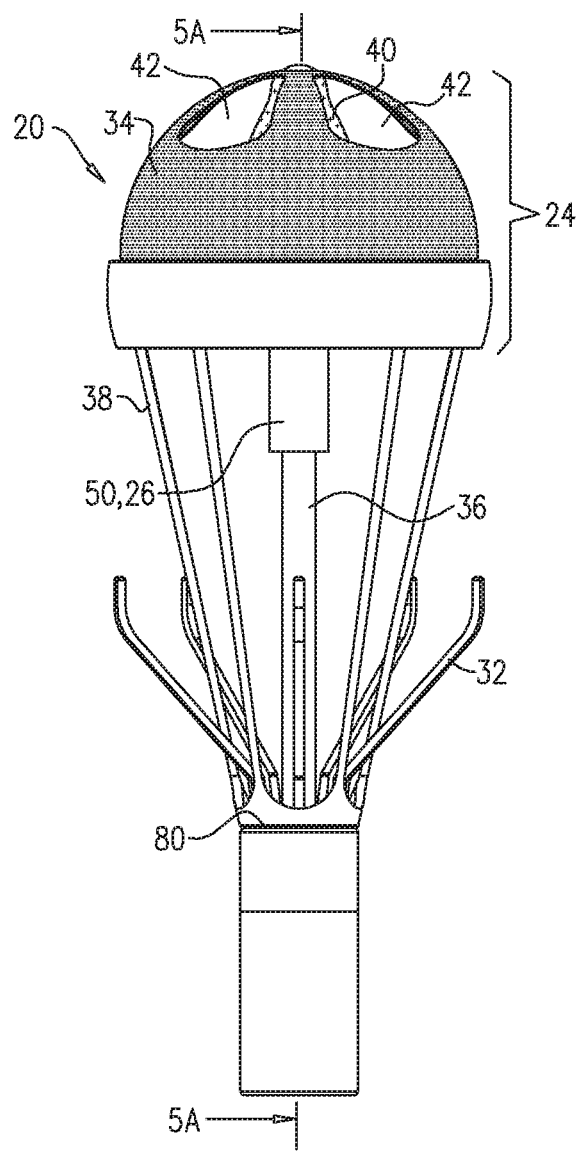
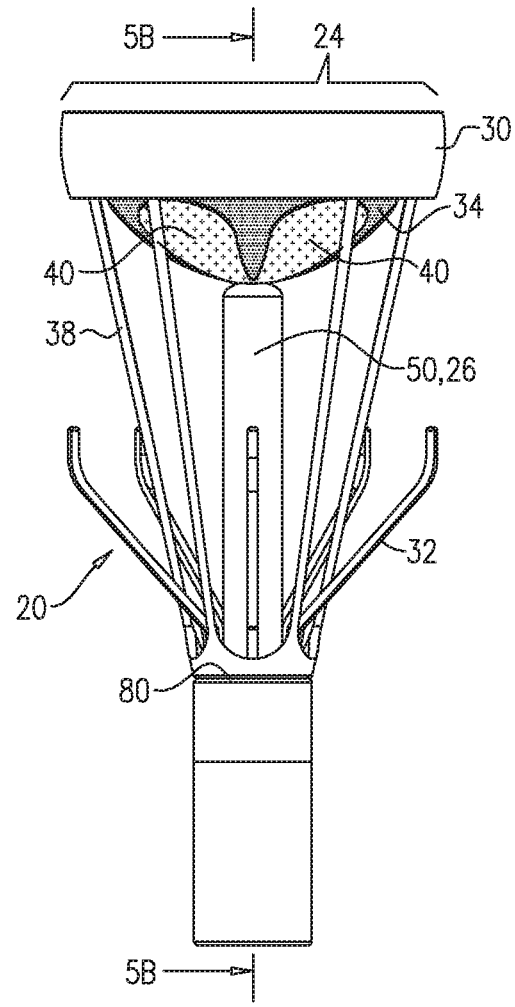
FIG. 2A
FIG. 2B
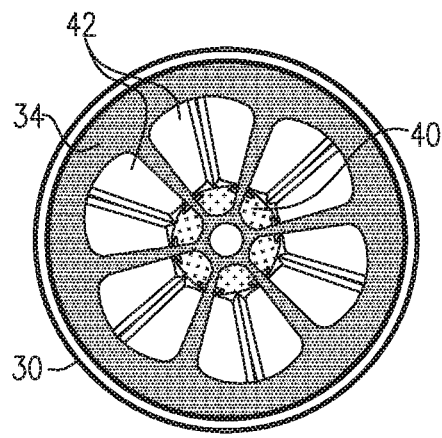
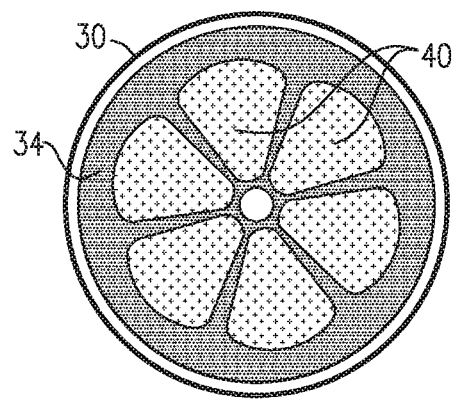
FIG. 3A
FIG. 3B

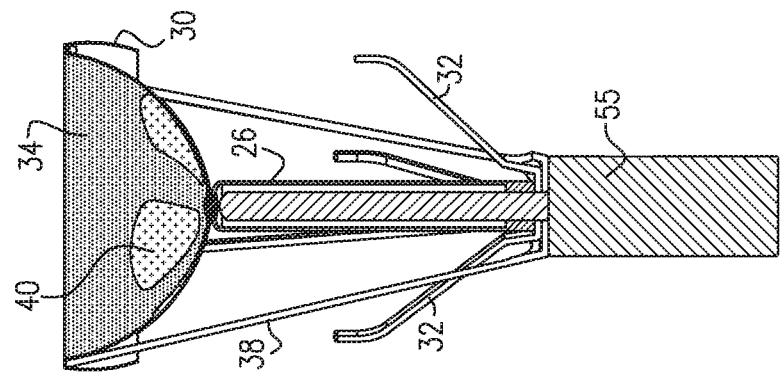
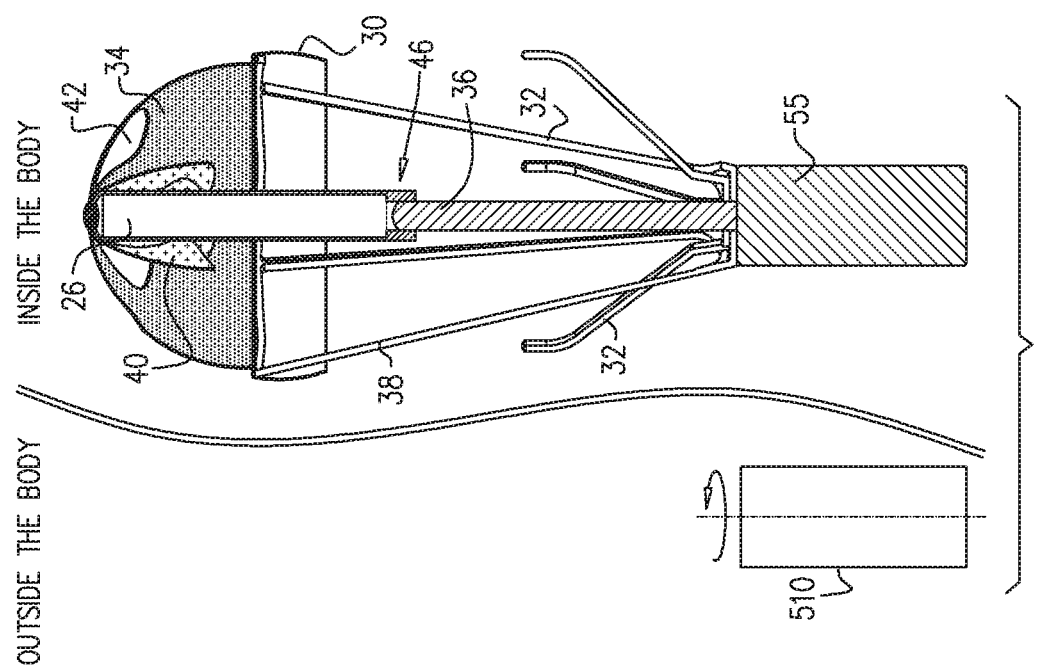
FIG. 5B
FIG. 5A

RECIPROCATING INTRAVASCULAR BLOOD PUMP

FIELD OF THE INVENTION

Some applications of the invention relate generally to medical procedures and implantable devices. More specifically, some applications of the invention relate to the use of a mechanical device for deployment in the circulatory system.

BACKGROUND

Cardiovascular disease is one of the leading causes of death. Blood pumps for insertion into the vasculature of a patient have been developed to provide mechanical circulatory support by supplementing the blood pumping action of a damaged or diseased heart. An example of an intravascular blood pump is the intra-aortic balloon pump, which is a pneumatic device typically deployed in an aorta of a patient to augment the pumping action of the heart. Typically, the aortic balloon pump includes a balloon, which inflates and deflates in a predetermined synchronous pattern with respect to the diastole and systole of the patient (inflates during diastole and deflates during systole). The aortic balloon pump typically inflates during diastole, thereby increasing coronary flow in the coronary arteries, and deflates during systole, thereby increasing blood flow forward in the aorta.

SUMMARY OF THE INVENTION

In accordance with some applications of the present invention, apparatus is provided for deployment in a lumen of a blood vessel of a subject. The apparatus typically affects blood flow in the blood vessel and improves circulation.

In accordance with some applications of the present invention, the apparatus comprises a reciprocating device, which moves downstream and upstream in the blood vessel in a reciprocating pattern to provide a first effective surface area when the apparatus moves downstream and a second effective surface area when the apparatus moves upstream. Typically, when the reciprocating device assumes the first effective surface area, blood is pushed downstream in the blood vessel during downstream motion of the reciprocating device. Typically, the first effective surface area is larger for pushing blood in the blood vessel than the second effective surface area.

For some applications, the apparatus comprises a pump portion comprising an anchor and a reciprocating valve. The anchor is configured to engage a wall of the blood vessel in order to maintain the apparatus in place within the blood vessel, and the reciprocating valve is coupled to the anchor and shaped to define a set of one or more leaflets. The apparatus further comprises a valve driver configured to drive the valve in a reciprocating pattern between (i) a first state in which the leaflets are in an open configuration allowing blood flow through the valve, and (ii) a second state in which the leaflets are in a closed configuration inhibiting blood flow through the valve. During upstream motion of the valve, when the leaflets are in the first state, the motion of the valve has a relatively small effect on blood flow. During downstream motion of the valve, when the leaflets are in the second state, the motion of the valve has a substantial effect on blood flow, driving blood in a downstream direction in the aorta.

There is therefore provided, in accordance with some applications of the present invention, apparatus configured to be deployed in a lumen of a blood vessel of a subject, the apparatus including:

a reciprocating device configured to move downstream and upstream in the blood vessel in a reciprocating pattern to provide:
  a first effective surface area of the device for pushing blood downstream in the blood vessel during downstream motion of the reciprocating device, and
  a second effective surface area of the device during upstream motion of the reciprocating device, the first effective surface area being larger for pushing blood in the blood vessel than the second effective surface area; and
a device driver configured to drive the reciprocating device in the reciprocating pattern.

For some applications, the reciprocating device includes a flexible membrane.

There is further provided, in accordance with some applications of the present invention, apparatus configured to be deployed in a lumen of a blood vessel of a subject, the apparatus including:

a pump portion including:
  an anchor configured to engage a wall of the blood vessel in order to maintain the apparatus in place within the blood vessel; and
  a reciprocating valve coupled to the anchor and shaped to define a set of one or more leaflets; and
a valve driver configured to drive the valve in a reciprocating pattern between:
  (i) a first state in which the leaflets are in an open configuration allowing blood flow through the valve, and
  (ii) a second state in which the leaflets are in a closed configuration inhibiting blood flow through the valve.

For some applications, the blood vessel is an aorta of the subject, and the apparatus is configured to be deployed in the aorta.

For some applications, the blood vessel is a vena cava of the subject, and the apparatus is configured to be deployed in the vena cava.

For some applications, the valve driver includes a rod (a) configured to be disposed parallel to a longitudinal axis of the blood vessel and downstream of the reciprocating valve when the apparatus is deployed in the blood vessel, and (b) configured to push the valve upstream in the blood vessel in the first state, and to pull the valve downstream in the blood vessel the second state.

For some applications, the apparatus does not include any leaflets for allowing and inhibiting blood flow in the blood vessel in addition to the set of one or more leaflets of the reciprocating valve.

For some applications, the apparatus does not include any leaflets that are configured to (a) open when the set of one or more leaflets of the reciprocating valve are in the closed configuration and (b) close when the set of one or more leaflets of the reciprocating valve are in the open configuration.

For some applications, the valve driver includes a diametric magnet.

For some applications, the valve driver includes a traverse roll.

For some applications, the valve driver is configured to drive the valve in the reciprocating pattern at a frequency of 1-5 Hz.

For some applications, the valve driver is configured to drive the valve in the reciprocating pattern at a frequency of 2-5 Hz.

For some applications, the valve driver is configured to drive the valve in the reciprocating pattern at a frequency that is higher than that of a beating heart.

For some applications, the reciprocating valve has thickness of 20-200 microns.

For some applications, the reciprocating valve includes a material selected from the group consisting of: polyurethane or polyethylene.

For some applications, the set of one or more leaflets includes 2-6 leaflets.

For some applications, the set of one or more leaflets is less flexible than the reciprocating valve.

For some applications, the set of one or more leaflets each have a thickness that is greater than a thickness of the reciprocating valve.

For some applications, the set of one or more leaflets are each shaped to define a near side and a far side and the far side has a thickness that is greater than a thickness of the near side.

For some applications, the anchor includes an O-ring anchor having an outer diameter of 15-30 mm.

For some applications, the anchor includes a first anchor and the apparatus further includes a second anchor downstream to the first anchor.

For some applications, the leaflets include a material selected from the group consisting of: polyurethane or polyethylene.

For some applications, the leaflets include animal tissue.

There is still further provided, in accordance with some applications of the present invention, a method including:

deploying in a lumen of a blood vessel of a subject, in a location that is downstream of a native aortic valve of a heart of the subject, a reciprocating valve shaped to define a set of one or more leaflets; and driving the valve in a reciprocating pattern between:
(i) a first state in which the leaflets are in an open configuration allowing blood flow through the valve, and
(ii) a second state in which the leaflets are in a closed configuration inhibiting blood flow through the valve.

For some applications, the blood vessel includes an aorta of the subject, and deploying the reciprocating valve includes deploying the reciprocating valve in the descending aorta.

For some applications, deploying the reciprocating valve in the blood vessel, includes anchoring the valve to the blood vessel using an anchor configured to engage a wall of the blood vessel.

For some applications, the method further includes not deploying any leaflets for allowing and inhibiting blood flow in the blood vessel in addition to the set of one or more leaflets of the reciprocating valve.

For some applications, driving the valve includes driving a rod: (a) to push the valve upstream in the blood vessel in the first state, and (b) to pull the valve downstream in the blood vessel in the second state.

For some applications, driving the rod includes driving the rod using a traverse roll mechanism.

The present invention will be more fully understood from the following detailed description of applications thereof, taken together with the drawings, in which:

BRIEF DESCRIPTION OF THE DRAWINGS

FIG. 1A is a schematic illustration of apparatus for deployment in a lumen of a blood vessel of a subject being deployed in the lumen, in accordance with some applications of the present invention;

FIGS. 1B and 1C are schematic illustrations of the apparatus being operated in the lumen of the blood vessel in a first state in which blood is allowed to flow through the apparatus (FIG. 1B), and a second state in which blood is inhibited from flowing through the apparatus (FIG. 1C), in accordance with some applications of the present invention;

FIGS. 2A and 2B are schematic illustrations of additional views of the apparatus in the first and second states, in accordance with some applications of the present invention;

FIGS. 3A and 3B are schematic illustrations of a top view of the apparatus in the first and second states, in accordance with some applications of the present invention;

FIGS. 5A and 5B are schematic illustrations of cross sections of the apparatus in the first and second states, and a power source for powering the apparatus, in accordance with some applications of the present invention;

DETAILED DESCRIPTION OF EMBODIMENTS

Figure 4B:
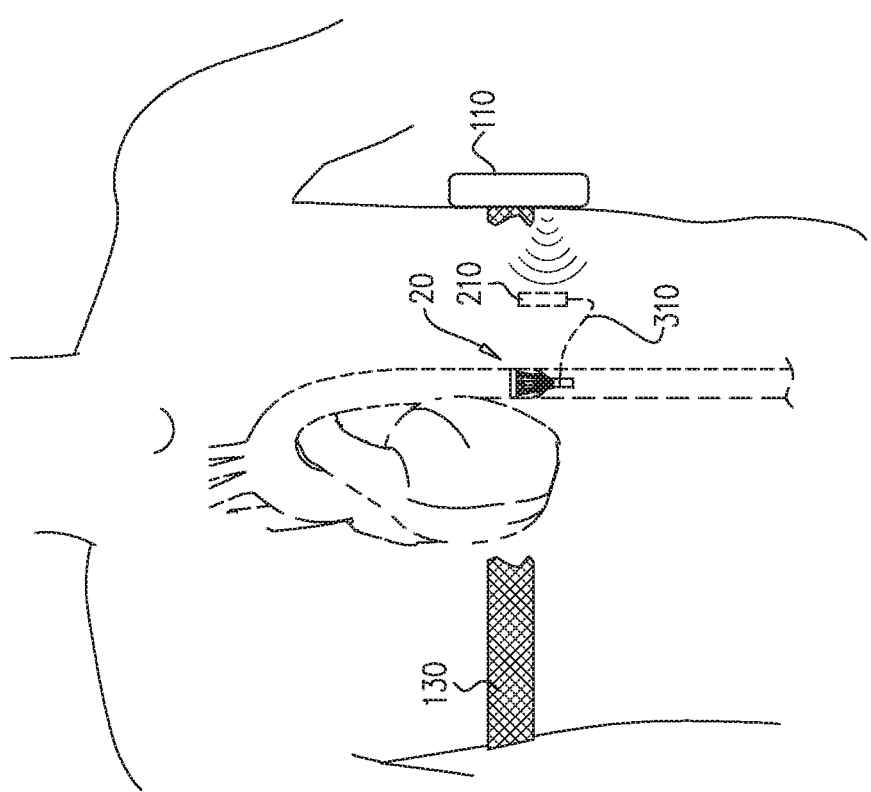
FIGS. 4A and 4B are schematic illustrations of the apparatus in the first and second states, and coupled to a power source for powering the apparatus, in accordance with some applications of the present invention.

Reference is first made to FIGS. 1A-C, which are schematic illustrations of apparatus 20 advanced and subsequently deployed in a lumen of a blood vessel 90 of a subject, in accordance with some applications of the present invention. Typically, apparatus 20 is advanced in the lumen of blood vessel 90 in a minimally-invasive procedure. Apparatus 20 is then deployed in a desired location in the blood vessel to facilitate blood flow in the blood vessel, as described hereinbelow. For example, apparatus 20 may be advanced in a delivery tool, e.g., a catheter 120, through a femoral artery in a retrograde direction and along the aorta until a desired location downstream of a native aortic valve is reached. Apparatus 20 is then deployed in the desired location in the aorta to improve blood flow in the aorta. As shown in FIG. 1A, apparatus is advanced in a retrograde direction in the aorta in a collapsed configuration. Upon reaching the desired location in the aorta (e.g., in the descending aorta), apparatus 20 begins operation, as illustrated in FIGS. 1B-C.

As shown in FIGS. 1B-C, for some applications, apparatus 20 comprises a pump portion 24 comprising an anchor 30 which engages a wall of blood vessel 90 in order to maintain apparatus 20 in place within blood vessel 90. Anchor 30 typically comprises an O-ring anchor having an outer diameter D1 of 15-30 mm, e.g., 20-30 mm.

Pump portion 24 further comprises a reciprocating device, e.g., reciprocating valve 34, coupled to anchor 30 and shaped to define a set of one or more leaflets 40, e.g., 2-6 leaflets 40. It is noted that for some applications, leaflets 40 are not shown to scale and may be larger in size than as shown in FIGS. 1B-C. When leaflets 40 are in an open configuration (for example as shown in FIG. 1B), valve 34 is shaped to define one or more windows 42 in place of where leaflets 40 are positioned in valve 34 when leaflets 40 are in a closed configuration (for example as shown in FIG.

1C). It is noted that for some applications, windows 42 are not shown to scale and may be larger in size than as shown in the figures.

Typically, valve 34 is a thin and flexible valve (e.g., a membrane) having a thickness T1 of 20-200 microns, e.g., 100-200 microns. Valve 34 is typically composed of a flexible material facilitating the reciprocating motion of valve 34, and due to its thinness, minimizing development of tension and compression in the flexible material during motion of valve 34. For example, valve 34 may comprise a biocompatible synthetic material, e.g., polyurethane or polyethylene. For other applications, valve 34 comprises a flexible, thin animal tissue.

For some applications, valve 34 may be similar to a known commercial valve, such as the Edwards Sapien™ valve, mutatis mutandis.

In contrast, leaflets 40 are typically less flexible than valve 34, and have a thickness that is greater than the thickness of valve 34. Leaflets 40 are typically thicker and less flexible than valve 34 in order to allow leaflets 40 to transition properly between open and closed configurations as described hereinbelow, and maintain a suitable seal with windows 42 of valve 34. For some applications, leaflets 40 are composed of animal tissue, e.g., porcine pericardium, which is typically a relatively thick membrane (e.g., on the order of 1-2 mm). Alternatively, leaflets 40 are composed of a biocompatible synthetic material such as polyurethane or polyethylene.

Apparatus 20 further comprises a valve driver 50 configured to drive valve 34 in a reciprocating pattern between a first state, shown in FIGS. 1B and 2A, in which leaflets 40 are in an open configuration, and a second state shown in FIGS. 1C and 2B, in which leaflets 40 are in a closed configuration. Typically, in the first state when leaflets 40 are in an open configuration, blood is allowed to flow through valve 34. In the second state, when leaflets 40 are in the closed configuration, blood is typically inhibited from flowing through valve 34. In the first state (FIG. 1B), valve driver 50 typically pushes valve 34 upstream in blood vessel 90, causing opening of leaflets 40 and allowing blood flow through valve 34 in a downstream direction in blood vessel 90. In the second state (FIG. 1C), valve driver 50 typically pulls valve 34 downstream in blood vessel 90, causing closing of leaflets 40 and inhibiting blood flow through valve 34 in a downstream direction in blood vessel 90. In the transition between the first state (FIG. 1B) and the second state (FIG. 1C), the motion of valve 34 being pulled downstream by valve driver 50 pushes blood downstream in blood vessel 90, thereby affecting blood flow in blood vessel 90.

Typically, in the second state in which reciprocating valve 34 is pulled downstream and leaflets 40 are in the closed configuration, valve 34 assumes a first effective surface area of valve 34 for pushing blood downstream in blood vessel 90, due to the orientation of the leaflets. In the first state in which reciprocating valve 34 is pushed upstream and leaflets 40 are in the open configuration, valve 34 assumes a second effective surface area of valve 34 (having a relatively small effect on blood flow). The first effective surface area is typically larger than the second effective surface area, and has a substantial effect on blood flow, driving blood in a downstream direction in the aorta by pushing the blood.

For some applications, valve driver 50 comprises a rod 26 configured to be disposed parallel to a longitudinal axis of the blood vessel and downstream of reciprocating valve 34 when apparatus 20 is deployed in blood vessel 90. Rod 26 pushes valve 34 upstream in the blood vessel in the first state, and pulls valve 34 downstream in blood vessel 90 in the second state. Typically, but not necessarily, reciprocating valve 34 assumes a convex configuration (as viewed from upstream of valve 34) when rod 26 pushes valve 34 upstream in blood vessel 90 in the first state, and a concave configuration when rod 26 pulls valve 34 downstream in blood vessel 90 in the second state.

Valve 34 typically affects blood flow in blood vessel 90 by reciprocation between the first state in which rod 26 pushes valve 34 upstream and leaflets 40 are in the open configuration, and the second state, in which rod 26 pulls valve 34 downstream and the leaflets are in the closed configuration. The reciprocating motion of valve 34 typically pushes the blood downstream in blood vessel 90, thereby assisting functioning of the heart. For example, apparatus 20 may be deployed in an aorta of the subject in a location that is downstream of a native aortic valve of the subject, e.g., in a descending aorta of the subject (although it is noted that apparatus 20 may be deployed in the aorta in a location that is closer to the native aortic valve, or elsewhere in the circulatory system). Operating apparatus 20 in the aorta typically increases blood flow in the aorta and reduces pressure in the ascending aorta (upstream of the valve 34).

Typically, apparatus 20 is not operated in coordination with a cardiac cycle of the subject. Thus, apparatus 20 typically does not comprise any heart rate or cardiac cycle sensor (such as an electrode for sensing the heart rate or the cardiac cycle). For example, the reciprocating motion of valve 34 (pushing of valve 34 upstream and pulling of valve 34 downstream) is typically not dependent on the frequency of heart beats, and is typically not operated in a synchronous pattern with respect to the diastole and systole of the subject. Typically, apparatus 20 is operated such that the reciprocating motion of valve 34 is at a frequency that is higher than that of a beating heart. For example, apparatus 20 operates at a reciprocating frequency of 1-5 Hz, e.g., 2-5 Hz.

It is noted that FIGS. 1A-C show blood vessel 90 as the aorta and apparatus 20 is shown in the aorta by way of illustration and not limitation. For some applications, apparatus 20 is deployed in another blood vessel 90, e.g., a vena cava of the subject.

Reference is now made to FIGS. 2A-B, which are schematic illustrations of additional views of apparatus 20, in accordance with some applications of the present invention. FIG. 2A shows a side view of apparatus 20 in the first state, with leaflets 40 in the open configuration, and FIG. 2B shows a side view of apparatus 20 in the second state in which leaflets 40 are in the closed configuration.

It is noted that apparatus 20 typically does not comprise any leaflets that are configured to (a) open when the set of one or more leaflets 40 of reciprocating valve 34 are in the closed configuration and (b) close when the set of one or more leaflets 40 of reciprocating valve 34 are in the open configuration. Indeed, apparatus 20 typically does not comprise any leaflets for allowing and inhibiting blood flow in the blood vessel, in addition to the set of one or more leaflets 40 of reciprocating valve 34.

For some applications, apparatus 20 comprises a second anchor positioned downstream of anchor 30 and configured to engage the wall of blood vessel 90 to anchor apparatus 20 to the wall of blood vessel 90. For some applications, the second anchor comprises a plurality of ribs 32, e.g., 2-6 ribs 32.

For some applications, apparatus 20 additionally comprises a plurality of self-expandable support members 38 extending from a base portion 80 of apparatus 20 to anchor 30. Support members 38 are typically shaped so that apparatus 20 is retrievable. For some applications, support members 38 are arranged in the form of a stent (and not as shown in the figures).

Reference is now made to FIGS. 3A-B, which are top views of apparatus 20, in accordance with some applications of the present invention. FIG. 3A shows a top view of apparatus 20 in the first state with leaflets 40 in the open configuration and wrapped around rod 26, allowing blood flow through valve 34. FIG. 3B shows a top view of apparatus 20 in the second state in which leaflets 40 are in the closed configuration and blood is inhibited from flowing through valve 34.

Figure 4A:
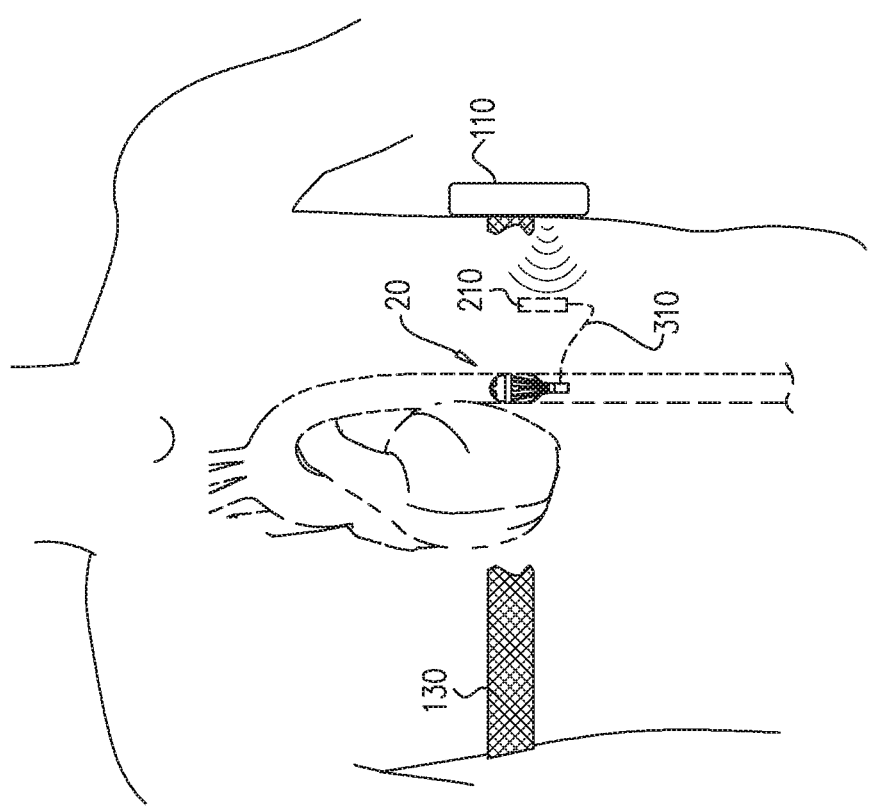

Reference is now made to FIGS. 4A-B, which are schematic illustrations of apparatus 20 in the first state (FIG. 4A) and in the second state (FIG. 4B). FIGS. 4A-B additionally show a power source for powering valve driver 50, for driving reciprocating valve 34. For some applications, apparatus 20 is powered by a radiofrequency (RF)-based system illustrated in FIGS. 4A-B. For such applications, at least one transmitter coil 110 is disposed outside the subject's body, and at least one receiver coil 210 is implanted in the subject. Transmitter coil 110 typically generates power of 3 kHz-14 MHz, e.g., 6-8 MHz or 13-14 MHz.

As shown in FIGS. 4A-B, external RF transmitter coil 110 is coupled to the subject (e.g., by a chest-band 130). RF transmitter coil 110 induces current in RF receiver coil 210 which is typically implanted subcutaneously in the subject. Power is typically carried through a wire 310 from receiver coil 210 to a motor of valve driver 50 in apparatus 20. Valve driver 50 in turn drives rod 26 in an upstream and downstream direction to push and pull valve 34 upstream and downstream in the blood vessel.

Reference is now made to FIGS. 5A-B, which are cross sections of apparatus 20, in accordance with some applications of the present invention. FIG. 5A shows a cross section of apparatus 20 in the first state with leaflets 40 in the open configuration and wrapped around rod 26, allowing blood flow through valve 34. FIG. 5B shows a cross section of apparatus 20 in the second state in which leaflets 40 are in the closed configuration and blood is inhibited from flowing through valve 34.

For some applications, valve driver 50 comprises a diametric magnet 55, which causes rotation of longitudinal element 36 which drives rod 26 in an upstream and downstream direction in blood vessel 90. For some applications, rod 26 is reciprocally driven by a traverse roll mechanism 46 operating between longitudinal element 36 and rod 26. Additionally, or alternatively, an extracorporeal rotating magnet 510 drives intracorporeal diametric magnet 55 to rotate, thus rotating longitudinal element 36 and driving rod 26 upstream and downstream in blood vessel 90.

Reference is now made to FIGS. 1A-C, 2A-B, 3A-B and 5A-B. Anchor 30 is shown in the drawings as a ring anchor (e.g., an O-ring) by way of illustration and not limitation. For some applications, apparatus 20 is maintained in place in blood vessel 90 by an alternative type of anchor. For example, apparatus 20 may be anchored to a wall of blood vessel 90 by a soft porous material, e.g., a suitable gauze, which at first absorbs blood but over time becomes less soft and generally impermeable to blood due to clotting of the blood therein.

Figure 6A:
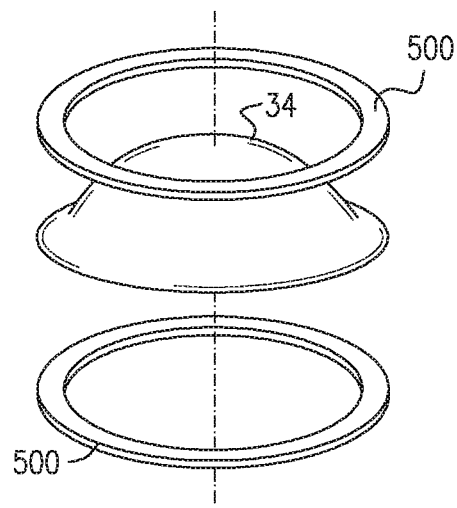
FIGS. 6A, 6B, and 6C are schematic illustrations of reciprocating valve, in accordance with some applications of the present invention.
Figure 6B:
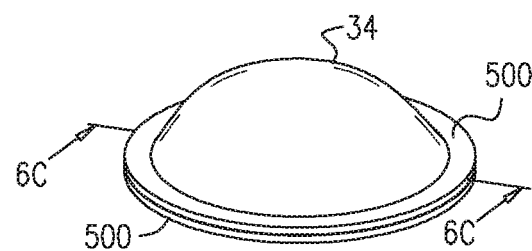
Figure 6C:
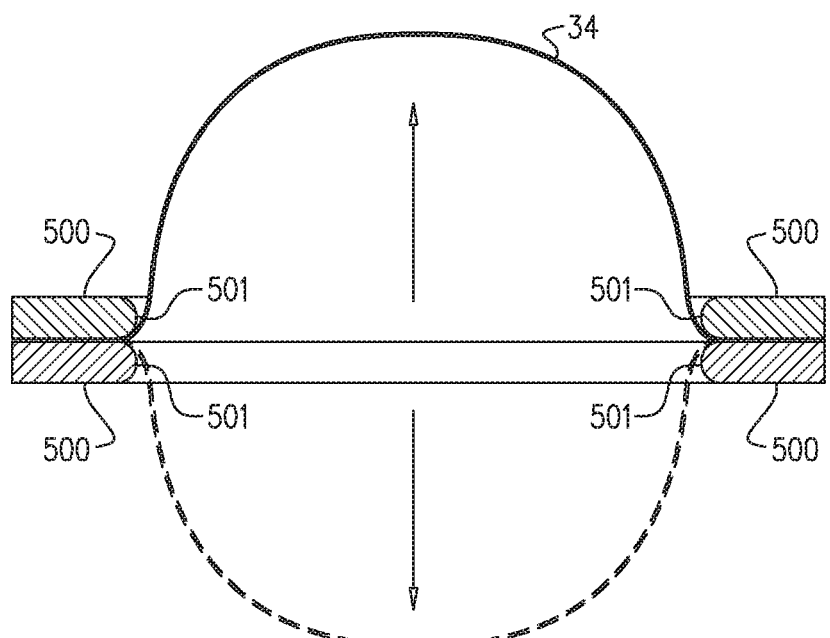

Reference is now made to FIGS. 6A-C, which are schematic illustrations of valve 34 in accordance with some applications of the present invention. Typically, valve 34 is clamped between two toroidal plates, e.g., washers 500, such that the edge along the perimeter of valve 34 is compressed between washers 500. Typically, washers 500 are composed of silicone, or another suitable, resilient material (which is typically slightly flexible, but may alternatively be rigid). Clamping valve 34 between washers 500 typically secures valve 34 and facilitates anchoring of valve 34 to anchor 30. As shown in the cross section in FIG. 6C, each washer 500 is shaped to define a rounded inner edge 501 in order to reduce any damage to valve 34 during the reciprocating motion of valve 34. (Leaflets 40 and windows 42 are not shown in FIGS. 6A-C).

Figure 7:
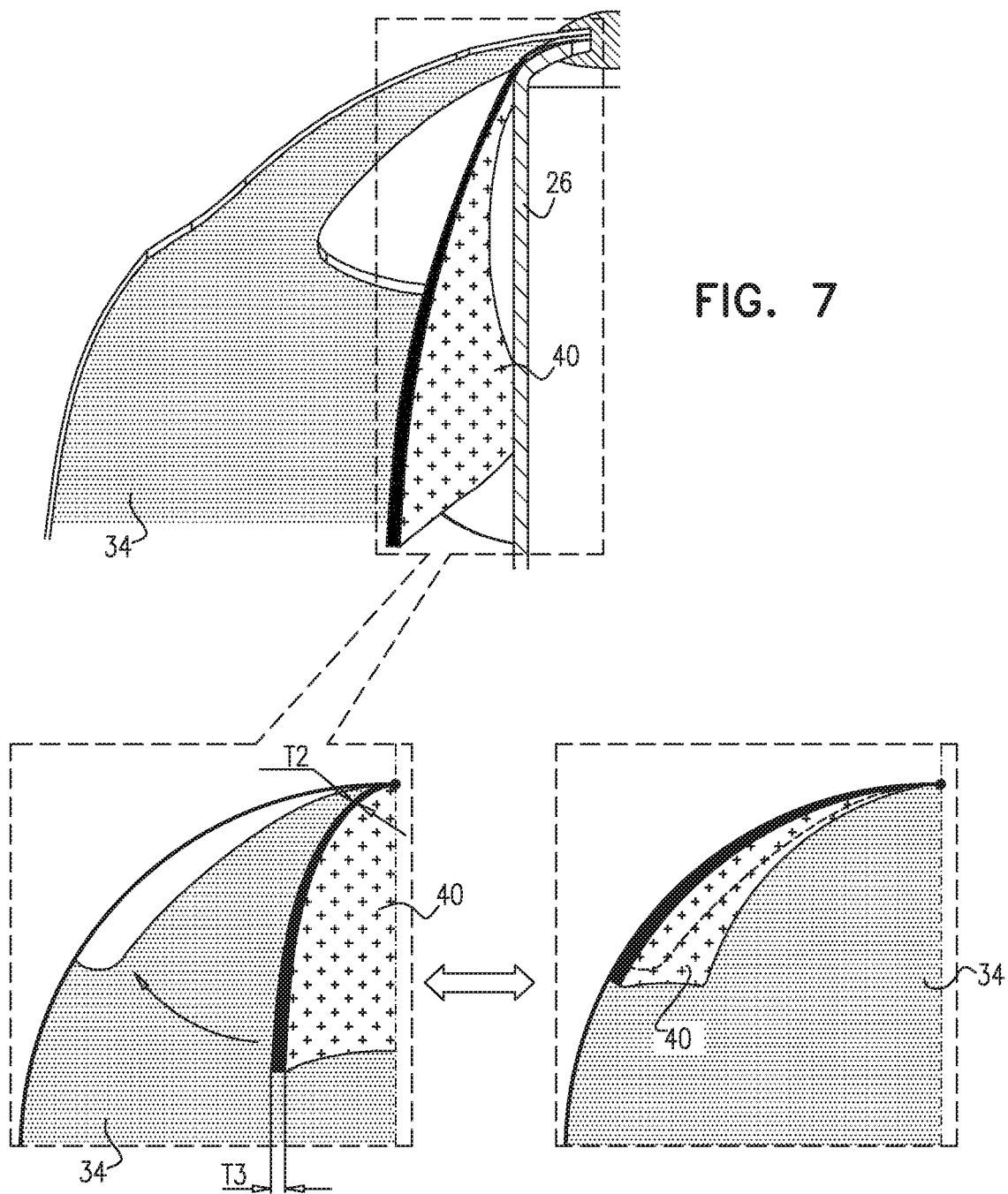
FIG. 7 is a schematic illustration of leaflets of the apparatus, in accordance with some applications of the present invention.

Reference is now made to FIG. 7, which is a schematic illustration of leaflets 40 in accordance with some applications of the present invention. As described hereinabove with reference to FIGS. 1B-C, the overall thickness of leaflets 40 is greater than that of valve 34. Additionally, for some applications, the thickness of leaflet 40 in a near side of the leaflet (the near side being the side that is coupled to valve 34) is less than a thickness of the leaflet at a far side of the leaflet (the far side being the side of the leaflet that is farther away from the coupling point of the leaflet with valve 34). Typically, the thickness of leaflet 40 increases as it extends away from the coupling point between valve 34 and leaflet 40. As shown in FIG. 7, leaflet 40 has a first thickness T2 at, or near, the coupling point with valve 34. As leaflet 40 extends away from the coupling point with valve 34, the thickness thereof increases gradually to a thickness T3. Leaflet 40 is typically thinner at the coupling point with valve 34 in order to provide the leaflet with greater flexibility at the coupling point, to allow for easy motion of leaflets 40 at the coupling point. The increased thickness T3 of leaflets 40 facilitates proper placement of leaflets 40 against windows 42.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus configured to be deployed in a lumen of a blood vessel of a subject, the apparatus comprising:
   a reciprocating device configured to move downstream and upstream in the blood vessel in a reciprocating pattern to provide:
   a first effective surface area of the device for pushing blood downstream in the blood vessel during downstream motion of the reciprocating device, and
   a second effective surface area of the device during upstream motion of the reciprocating device, the first effective surface area being larger for pushing blood in the blood vessel than the second effective surface area; and
   a device driver configured to drive the reciprocating device in the reciprocating pattern at a frequency of 2-5 Hz.

2. The apparatus according to claim 1, wherein the reciprocating device comprises a flexible membrane.

3. The apparatus according to claim 1, wherein the blood vessel is an aorta of the subject, and wherein the apparatus is configured to be deployed in the aorta.

4. The apparatus according to claim 1, wherein the apparatus is not configured to coordinate the reciprocating pattern with a cardiac cycle of the subject.

5. The apparatus according to claim 1, wherein the apparatus does not comprise any sensor of heart rate or cardiac cycle.

\* \* \* \* \*